United States Patent [19]

Hoehn et al.

[11] 4,293,649

[45] Oct. 6, 1981

[54] PROCESS FOR PRODUCTION OF ANTIBIOTIC A-33853

[75] Inventors: Marvin M. Hoehn; Karl H. Michel, both of Indianapolis, Ind.

[73] Assignee: Eli Lilly and Company, Indianapolis, Ind.

[21] Appl. No.: 123,330

[22] Filed: Feb. 21, 1980

[51] Int. Cl.³ .............................................. C12P 17/16
[52] U.S. Cl. ................................... 435/118; 435/169; 435/886; 546/270
[58] Field of Search ............................... 435/118, 169

[56] References Cited

PUBLICATIONS

Dolak et al., The Journal of Antibiotics, vol. 33, No. 11, pp. 1391–1393 (Nov. 1980).
Kimura et al., The Journal of Antibiotics, vol. 23, No. 9, pp. 461–463 (Sep. 1970).

*Primary Examiner*—Lionel M. Shapiro
*Attorney, Agent, or Firm*—Dwight E. Morrison; Arthur R. Whale

[57] ABSTRACT

Antibiotic A-33853 is produced by submerged, aerobic fermentation of a new Streptomyces sp. NRRL 12068. The antibiotic has shown antibacterial activity against Staphylococcus and Streptococcus species which are penicillin resistant. In addition, the antibiotic has shown antiviral and antitrichomonal activity in vitro.

2 Claims, 2 Drawing Figures

PROCESS FOR PRODUCTION OF ANTIBIOTIC A-33853

BACKGROUND OF THE INVENTION

1. Field of the Invention

A large variety of pathogenic microorganisms, such as bacteria and protozoa, and causative agents in producing diseased states in man and animals.

Included in the list of causative agents are such organisms as *Staphylococcus aureus*, *Salmonella typhosa*, and *Pasteurella multocida*, the last being epidemiologically associated with pneumonia in sheep and cattle. *Mycoplasma gallisepticum* and other Mycoplasma cause respiratory problems in chickens and turkeys.

Although a number of antibiotics have been developed, some of which possess activity against one or more pathogenic organisms, there remains a need for more effective agents to combat the many diseases caused by these organisms in man and animals.

2. Description of the Prior Art

The A-33853 antibiotic belongs to a new class of antibiotics.

SUMMARY OF THE INVENTION

This invention relates to antibiotic substance A-33853 and to the tetraacetyl derivative thereof.

The A-33853 antibiotic is produced by culturing Streptomyces sp. NRRL 12068, or an A-33853-producing mutant or variant thereof, under submerged aerobic fermentation conditions.

Antibiotic A-33853 inhibits the growth of certain pathogenic microorganisms, as well as a number of viral organisms. The antibiotic A-33853 and its tetraacetyl derivative both show in vitro activity against *Trichomonas vaginalis*.

DESCRIPTION OF THE DRAWINGS

The infrared absorption spectra of antibiotic A-33853 and the tetraacetyl derivative of A-33853 are presented in the accompanying drawings, as follows.

DETAILED DESCRIPTION OF THE INVENTION

This invention relates to a novel antibiotic substance having the following formula

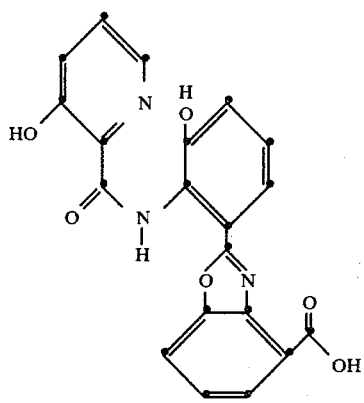

and to its preparation. The compound represented by the above structural formula is named, according to Chemical Abstracts nomenclature rules, as 2-[3-hydroxy-2-[[(3-hydroxy-2-pyridinyl)carbonyl]amino]-phenyl]-4-benzoxazolecarboxylic acid. For convenience, this new antibiotic is designated herein as A-33853.

This A-33853 antibiotic is produced by culturing the previously undescribed microorganism Streptomyces sp. NRRL 12068, or an A-33853-producing mutant or variant thereof, in a culture medium containing assimilable sources of carbon, nitrogen, and inorganic salts, under submerged aerobic fermentation conditions until a substantial amount of antibiotic activity is produced. The fermentation mixture is filtered to remove the biomass, i.e., the mycelia, and the pH of the filtrate adjusted to a pH of about 6 to about 7, preferably about pH 6.5. The antibiotic is then isolated from the filtered fermentation broth preferably by extraction with an organic solvent, such as chloroform, and concentration of the extract. Other solvents suitable for use in this extraction step include ethyl acetate, methyl acetate, n-butanol, and related water-immiscible polar solvents.

Antibiotic A-33853 is a light yellow-green, crystalline compound, having a melting point of about 315° C. (dec.). The antibiotic has a molecular weight of 391, as determined by electron-impact mass spectrometry, and an approximate elemental analyses as follows: 61.21 percent carbon, 3.18 percent hydrogen, 10.64 percent nitrogen, and 24.77 percent oxygen. Based on elemental analysis and molecular weight, an empirical formula of $C_{20}H_{13}N_3O_6$ is assigned to antibiotic A-33853. Potentiometric titration of the novel antibiotic in 66 percent dimethylformamide in water indicated the presence of three titratable groups with $pK_a$ values of about 7.25, 10.0, and 12.21 (initial pH 5.0). The titration results indicate the antibiotic is capable of forming salts, for example with the alkali metals and ammonium.

Antibiotic A-33853 has no specific rotation at $[\alpha]_D^{25°}$ and $[\alpha]_{365}^{25°}$.

Figure 1:
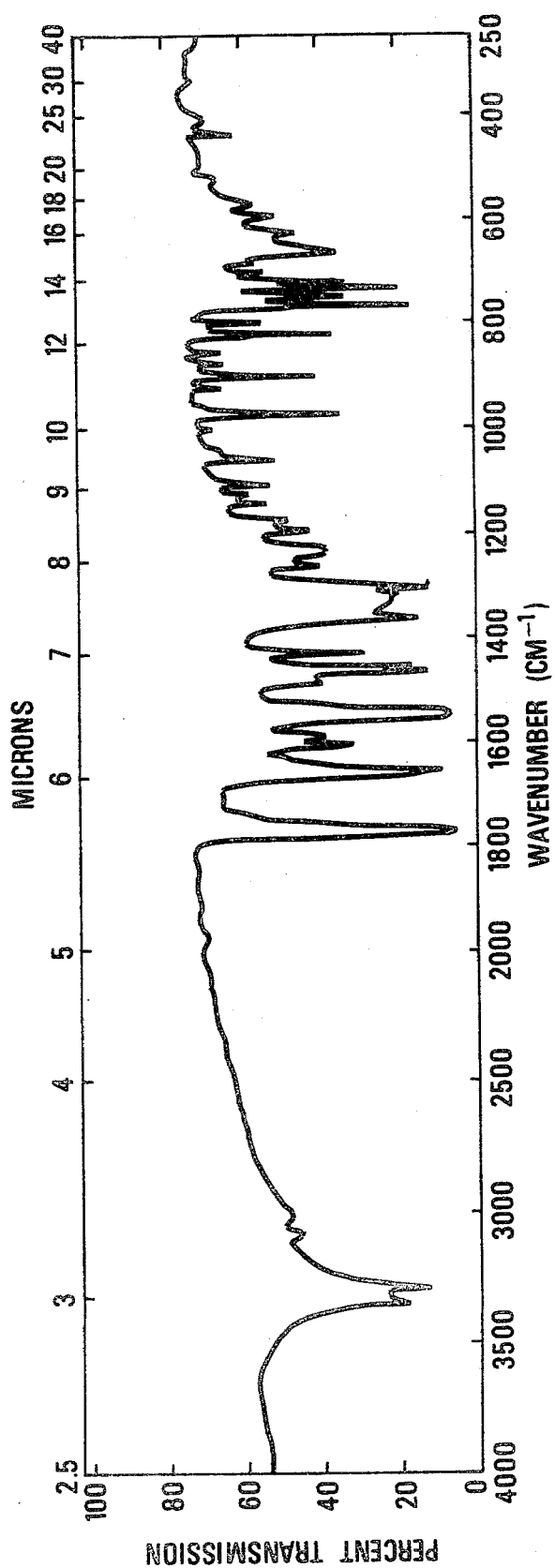
FIG. 1: A-33853 (in KBr pellet)

The infrared absorption spectrum of antibiotic A-33853 in KBr pellet is shown in the accompanying drawings as FIG. 1. The following distinguishable absorption maxima are observed: 3338, 3280, 3080 (very weak), 2990 (very weak), 1760, 1646, 1595 (weak), 1583 (very weak), 1534, 1457, 1449 (shoulder), 1422, 1359, 1312, 1298, 1254 (weak), 1227 (weak), 1186 (weak), 1170 (weak), 1133 (weak), 1120 (weak), 1100 (weak), 1050, 990 (very weak), 961, 912 (weak), 893, 867 (weak), 848 (weak), 819 (shoulder), 810, 789 (weak), 762 (shoulder), 756, 739, 720, 710, 691 (weak), 675 (very weak), 654, 622, 593 (weak), 579 (weak), 531 (very weak), 509 (very weak), 473 (weak), 443 (very weak), and 375 (very weak) cm$^{-1}$.

The ultraviolet absorption spectra of antibiotic A-33853 in both neutral and acidic dioxane exhibit absorption maxima at 250 nm (shoulder, $\epsilon$ 18,000), 313 nm ($\epsilon$ 28,300) and 322 nm (shoulder, $\epsilon$ 28,000). The ultraviolet spectrum in basic dioxane shows absorption maxima at 254 nm ($\epsilon$ 39,000), 310 nm ($\epsilon$ 17,000), 360 nm ($\epsilon$ 11,000), and 400 nm ($\epsilon$ 10,500).

The $^{13}C$ nuclear magnetic resonance spectrum of antibiotic A-33853 in DMSOd$_6$, using internal TMS as reference, shows certain characteristics. The chemical shifts are expressed in parts per million (PPM), and are recorded in Table 1, which follows.

TABLE 1

| No. | 13CNMR/DMSO, Chemical Shift in PPM |
|---|---|
| | PPM |
| 1 | 167.5 |
| 2 | 165.8 |
| 3 | 162.6 |
| 4 | 157.2 |
| 5 | 153.2 |
| 6 | 150.4 |
| 7 | 140.3 |
| 8 | 140.1 |
| 9 | 131.2 |
| 10 | 129.3 |
| 11 | 127.8 |
| 12 | 126.5 |
| 13 | 125.9 |
| 14 | 124.9 |
| 15 | 123.5 |
| 16 | 122.9 |
| 17 | 122.5 |
| 18 | 120.6 |
| 19 | 119.7 |
| 20 | 114.5 |

The proton nuclear magnetic resonance spectrum of antibiotic A-33853, determined at 220 MHz (TMS standard), is set forth in Table 2, which follows:

TABLE 2

| Chemical Shifts in PPM | | | |
|---|---|---|---|
| Pyridine (ppm) | J (Hz) | DMSO (ppm) | J (Hz) |
| 8.32 | 1.8;4.1 | 8.32 | 1.0;4.0 |
| 8.28 | 1.2;7.7 | 7.90 | 1.0;7.8 |
| 7.95 | 1.8;7.5 | 7.81 | 1.0;7.8 |
| 7.70 | 1.2;8.0 | 7.71 | 1.5;7.5 |
| 7.45 | 1.8;7.5 | 7.60 | 4.5;8.0 |
| 7.38 | 8.0;8.0 | 7.48 | 8.0;8.0 |
| 7.35 | 8.0;8.0 | 7.46 | 1.0;8.0 |
| 7.26 | 1.5;8.1 | 7.42 | 8.0;8.0 |
| 7.20 | 4.0;8.1 | 7.26 | 1.5;8.0 |

Pure, crystalline antibiotic A-33853 is soluble in dimethylsulfoxide, chloroform, pyridine, and 0.1 N sodium hydroxide at 5 mg/ml, but is less soluble in acetone, methanol, ethyl acetate, tetrahydrofuran, and water.

Antibiotic A-33853, crystallized from a mixture of chloroform and methanol, has a characteristic X-ray powder diffraction pattern (copper radiation, 1.5418λ, nickel filter, d=interplanar spacing in angstroms) recorded in Table 3, which follows:

TABLE 3

X-Ray Powder Diffraction Characteristics of Antibiotic A-33853

| Spacing d(Å) | Relative Intensities I/I$_1$ |
|---|---|
| 16.36 | .10 |
| 12.63 | .19 |
| 10.65 | .14 |
| 9.51 | .81 |
| 8.31 | .24 |
| 6.61 | .05 |
| 6.17 | .19 |
| 5.68 | .48 |
| 5.32 | .62 |
| 4.82 | .19b* |
| 4.15 | .14b |
| 3.79 | .57 |
| 3.61 | 1.00 |
| 3.48 | 1.00 |
| 3.31 | .43 |
| 3.18 | .52 |
| 3.14 | .19 |
| 3.03 | .57 |

TABLE 3-continued

X-Ray Powder Diffraction Characteristics of Antibiotic A-33853

| Spacing d(Å) | Relative Intensities I/I$_1$ |
|---|---|
| 2.88 | .10 |
| 2.81 | .10 |
| 2.66 | .05 |
| 2.62 | .10 |
| 2.51 | .05 |
| 2.40 | .10 |
| 2.33 | .05 |
| 2.26 | .05 |
| 2.20 | .14 |
| 2.07 | .10 |
| 1.973 | .14 |

*b = broad

Antibiotic A-33853, on treatment with acetic anhydride in pyridine, forms a compound the structure of which is established to be the following

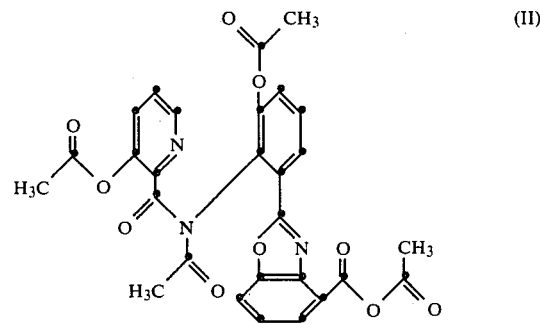

(II)

and which is named as: 2-[2-[acetyl[[3-(acetyloxy)-2-pyridinyl]carbonyl]amino]-3-(acetyloxy)phenyl]-4-benzoxazolecarboxylic acid, anhydride with acetic acid. Although it is realized that the carboxyl group of antibiotic A-33853 forms an anhydride with the acetic anhydride reagent, while the other active groups in the molecule form acetyl derivatives, the above compound is hereinafter referred to as the tetraacetyl derivative for convenience in terminology.

Following the same general procedure used in the preparation of the tetraacetyl derivative, other tetraacyl derivatives may be prepared, e.g., the tetraformyl, tetrapropionyl, tetrabutyryl, and tetrapentanoyl.

The tetraacetyl derivative of antibiotic A-33853 is a white, crystalline compound, having a melting point of about 184°–189° C. (from chloroform: ethanol), a molecular weight of 559, as determined by electron-impact mass spectrometry, and an approximate elemental analysis as follows: 59.85 percent carbon, 3.51 percent hydrogen, 7.73 percent nitrogen, and 28.50 percent oxygen.

Figure 2:
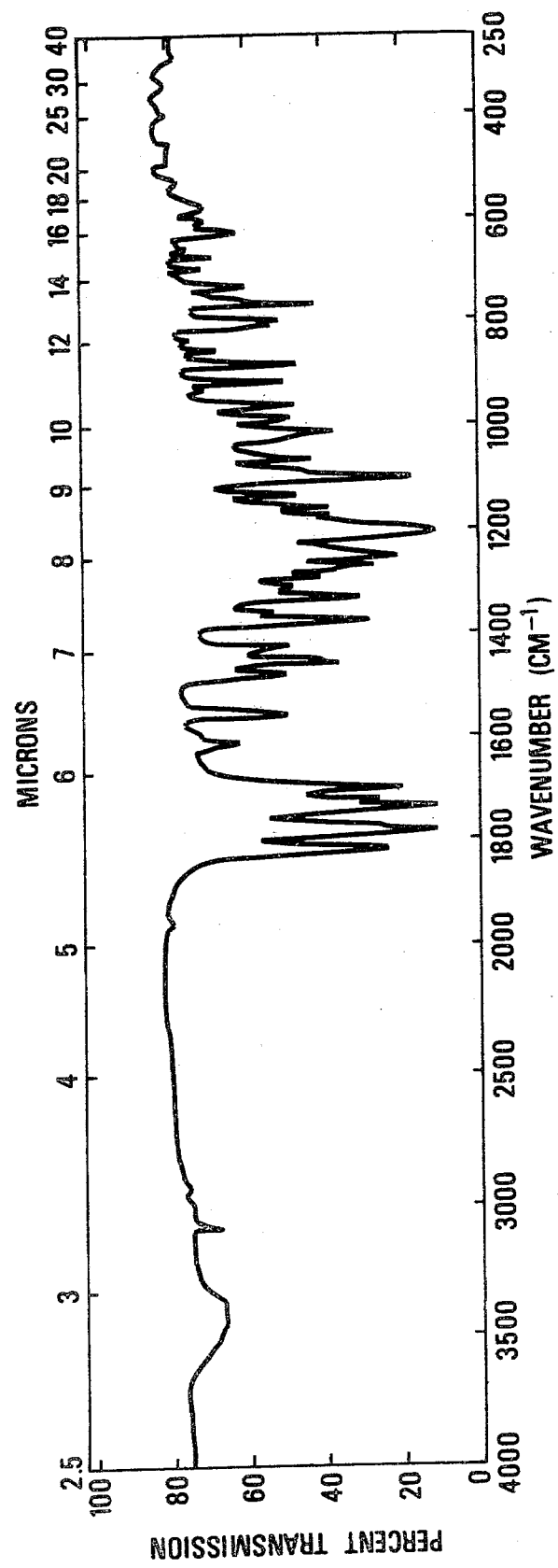
FIG. 2: Tetraacetyl derivative of A-33853 (in KBr pellet)

The infrared absorption spectrum of the tetraacetyl derivative of antibiotic A-33853 is shown in the accompanying drawings as FIG. 2. The following distinguishable maxima are observed: 3600–3200 (broad band), 3060 (weak), 2910 (very weak), 1951 (very weak), 1810, 1774, 1728, 1714, 1690, 1601 (weak), 1589 (very weak), 1549, 1471, 1452, 1441 (shoulder), 1418, 1369, 1350 (weak), 1322, 1301 (weak), 1282 (weak), 1271 (shoulder), 1261, 1254, 1215 (shoulder), 1197, 1163 (very weak), 1150, 1128, 1092, 1059, 1003, 981, 955, 916 (weak), 910, 873, 849 (weak), 820 (very weak), 800 (shoulder), 792, 760, 752 (shoulder), 729, 690 (weak), 670 (weak), 655 (very weak), 622, 603 (weak), 580 (weak), 531 (weak), 490 (very weak), 476 (weak), 420 (weak), 403 (very weak), 370 (very weak), 360 (very weak), 330 (very weak), and 310 (weak) cm$^{-1}$.

The ultraviolet absorption spectra of the tetraacetyl derivative of antibiotic A-33853 in both neutral and acidic dioxane exhibit maxima at 270 nm (shoulder, $\epsilon$ 18,000) and 320 nm ($\epsilon$ 29,000), while the ultraviolet absorption spectrum in basic dioxane shows absorption maxima at 254 nm ($\epsilon$ 40,000), 310 nm ($\epsilon$ 18,000), 365 nm ($\epsilon$ 12,000), and 400 nm ($\epsilon$ 11,000).

The proton nuclear magnetic resonance spectrum of the tetraacetyl derivative of antibiotic A-33853, determined at 220 MHz (TMS standard), is set forth in Table 4, which follows:

TABLE 4

| Chemical Shifts in PPM | |
|---|---|
| CDCl$_3$ (ppm) | J (Hz) |
| 8.26 | 1.5;4.4 |
| 8.24 | — |
| 8.08 | 1.0;7.8 |
| 7.86 | 1.1;8.1 |
| 7.58 | 7.8;7.8 |
| 7.50 | 1.3;8.0 |
| 7.50 | 1.3;8.0 |
| 7.46 | 8.0;8.0 |
| 7.33 | 4.5;8.2 |

The X-ray powder diffraction characteristics of the tetraacetyl derivative of antibiotic A-33853 (copper radiation, 1.5418$\lambda$, nickel filter, d=interplanar spacing in angstroms) are recorded in Table 5, which follows:

TABLE 5

| X-Ray Diffraction Characteristics of the Tetraacetyl Derivative of Antibiotic A-33853 | |
|---|---|
| Spacing d(Å) | Relative Intensities I/I$_1$ |
| 8.12 | 1.00 |
| 7.63 | .09 |
| 7.17 | .45 |
| 6.44 | .18 |
| 6.22 | .09 |
| 5.52 | .27 |
| 5.14 | .18 |
| 4.91 | .36 |
| 4.61 | .45 |
| 4.32 | .27 |
| 4.06 | .36 |
| 3.88 | .09 |
| 3.67 | .55 |
| 3.53 | .27 |
| 3.36 | .18 |
| 3.14 | .18 |
| 2.93 | .18 |

The X-ray crystallographic unit-cell parameters for the tetraacetyl derivative of antibiotic A-33853 are set forth in Table 6, which follows:

TABLE 6

| Tetraacetyl A-33853 Crystallographic Parameters |
|---|
| C$_{28}$H$_{21}$N$_3$O$_{10}$         M.W. = 559 |
| a = 10.548 ± 0.001 A |
| b = 15.303 ± 0.003 A |
| c = 16.570 ± 0.003 A |
| $\beta$ = 101.13 ± 0.01 A |
| $\nu$ = 2624.4 ± 0.8 A |
| SPACE GROUP: P2$_1$/a |
| Z = 4 |

The tetraacetyl A-33853 has no specific rotation at $[\alpha]_D^{25°}$ and $[\alpha]_{365}^{25°}$.

Potentiometric titration of the tetraacetyl derivative of antibiotic A-33853 in 66 percent aqueous dimethylformamide showed no titratable groups present in the molecule.

This tetraacetyl derivative is soluble in pyridine and chloroform at 1 mg/ml, but is insoluble, or only sparingly soluble, in acetone, methanol, ethyl acetate, tetrahydrofuran, water, dimethyl sulfoxide, 0.1 N aqueous sodium hydroxide, and 0.1 N aqueous hydrochloric acid.

The Streptomyces sp. culture which is useful for the production of the A-33853 antibiotic, and which was initially isolated from a soil sample from Alaska, has been deposited and made a part of the stock culture collection of the Northern Regional Research Center, U.S. Department of Agriculture, Agricultural Research Service, Peoria, Ill. 61604, from which it is available to the public under the number NRRL 12068.

As is the case with other organisms, the characteristics of the A-33853-producing culture, Streptomyces sp. NRRL 12068, are subject to variation. For example, natural variants, mutants (spontaneous or induced), transconjugants and recombinants (including recombinant DNA on plasmids) of the NRRL 12068 strain, or derived from this strain, which produce the A-33853 antibiotic may be used in this invention.

A number of different media may be used to produce antibiotic A-33853 with Streptomyces sp. NRRL 12068. For economy in production, optimal yield, and ease of product isolation, however, certain culture media are preferred. Thus, for example, preferred carbon sources are glucose, dextrin, tapioca dextrin, corn starch, and glycerol. Optimum levels of carbon sources are from about 4 to about 8% by weight. Preferred nitrogen sources are enzyme-hydrolyzed casein, beef extract, soybean meal, and meat peptone. Cornmeal is useful in the fermentation media, but it is not clear if it serves as a source of carbon, nitrogen, minerals, or undefined growth factors.

Essential trace elements necessary for the growth and development of the organism may occur as impurities in other constituents of the media in amounts sufficient to meet the growth and biosynthetic requirements of the organism. However, it may be beneficial to incorporate in the culture media additional soluble nutrient inorganic salts capable of yielding sodium, potassium, magnesium, calcium, ammonium, chloride, carbonate, phosphate, sulfate, nitrate and like ions.

For producing substantial quantities of the A-33853 antibiotic, submerged aerobic fermentation in tanks is preferred. However, small quantities of the A-33853 antibiotic may be obtained by shake-flask culture. For tank fermentation, it is preferable to use a vegetative inoculum. The vegetative inoculum is prepared by inoculating a small volume of culture medium with the spore form, mycelial fragments, or a lyophilized pellet of the organism to obtain a fresh, actively growing culture of the organism. The vegetative inoculum is then transferred to a larger tank where, after a suitable incubation time, the A-33853 antibiotic is produced in optimal yield.

The A-33853-producing organism can be grown over a broad temperature range of from about 25° C. to about 43° C. Optimum production of A-33853 antibiotic appears to occur at a temperature of about 30° C.

As is customary in aerobic submerged culture processes, sterile air is dispersed through the culture medium. For efficient growth of the organism, the volume of the air used in tank production is in the range of from about 0.25 to about 10 volumes of air per volume of culture medium per minute (v/v/m), with from about 200 to about 400 RPM agitation. An optimum rate in a 165-liter vessel is about 0.5 v/v/m, with agitation provided by a propellar rotating at about 300 RPM. It may be necessary to add small amounts (i.e., 0.2 ml/L.) of an antifoam agent such as polypropylene glycol to large-scale fermentation media if foaming becomes a problem.

Antibiotic activity is generally present after about 24 hours and remains present for at least 4 days during the fermentation period. Peak antibiotic production occurs at from about 2 to about 4 days fermentation time.

Production of the A-33853 antibiotic can be monitored during the fermentation by either agar diffusion or turbidimetric methods. Test organisms suitable for use include *Staphylococcus aureus, Bacillus subtilis,* and *Micrococcus luteus.* The bioassay is preferably performed employing *Bacillus subtilis* in a paper disc agar diffusion plate test.

The A-33853 antibiotic can be recovered from the fermentation medium by methods used in the art. The A-33853 antibiotic is generally present in the broth. Maximum recovery of the A-33853 antibiotic is accomplished, therefore, by an initial filtration to remove the mycelial mass. The filtered broth can be purified by a variety of techniques to give the A-33853 antibiotic. A preferred technique involves adjustment of the pH of the filtered broth to a value of from about 5 to about 7, preferably to about pH 6.5, followed by extraction of the broth with a suitable solvent, for example, chloroform. Other solvents suitable for use in this extraction step include ethyl acetate, methyl acetate, n-butanol and related water-immiscible polar solvents. The extract is then concentrated to a small volume, whereupon a solid precipitate forms. The solid material is filtered off to give the antibiotic A-33853.

A first step in the purification of this solid material can be accomplished by dissolving the crude antibiotic A-33853 in a mixture of a water-soluble organic solvent, such as acetonitrile, and dilute aqueous base, e.g., 1 N aqueous sodium hydroxide, potassium hydroxide, or the like. The solution is then adjusted to about pH 6-7, using aqueous acid, for example, 1 N aqueous hydrochloric acid. The solution is then extracted with a water-immiscible solvent in which the antibiotic A-33853 is soluble, for example, chloroform. The chloroform extract is concentrated in vacuo to a small volume and then added to a large volume of a hydroxylic solvent such as methanol. This solution is then concentrated in vacuo until the antibiotic begins to precipitate. The concentrated solution is then allowed to stand for a few minutes at room temperature and when the precipitation is complete, the antibiotic is recovered by filtration.

The crude antibiotic A-33853 is further purified by crystallization from a suitable solvent or mixture of solvents, such as a mixture of chloroform and methanol, which yields the pure antibiotic A-33853.

Antibiotic A-33853 inhibits the growth in vitro of certain pathogenic microorganisms, in particular, some within the genera Staphylococcus and Streptococcus. Antibiotic A-33853 also inhibits the growth in vitro of a number of viral organisms, including Vaccinia, Polio virus type III, Herpes virus type I, Ann Arbor influenza virus type A, Echo 10, Maryland B influenza virus, and Rhino virus. The tetraacetyl A-33853 is active in vitro against Maryland B influenza virus.

In addition, antibiotic A-33853 is active in vitro against the protozoan organism *Eimeria tenella,* a major causative organism of coccidiosis.

Furthermore, A-33853 and its tetraacetyl derivative are active in vitro against *Trichomonas vaginalis.* Using the tube-dilution test, the minimal inhibitory concentration (MIC) of antibiotic A-33853 against *T. vaginalis* is less than 0.975 mcg/ml, while the MIC of tetraacetyl A-33853 against *T. vaginalis* is 125 mcg/ml.

The $LD_{50}$ of A-33853 in the mouse, IP, is greater than 300 mg/kg.

Antibiotic A-33853 is also active as a mosquito larvicide.

The levels at which antibiotic A-33853 inhibits the growth of organisms were determined using various testing procedures.

DISC-PLATE SCREENING PROCEDURE

Agar plates, inoculated with the test organism, were used; 6 mm. discs (0.02 ml. capacity) were saturated from log 2 dilutions of the antibiotic solution. Disc content was 1/5 or 1/50 of the concentration of the solution used, i.e., disc content of 300 µg. or 30 µg. was obtained from a solution of 1500 µg./ml. concentration. The size of the zone of inhibition produced by antibiotic A-33853 for each disc content is reported in Table 7, which follows:

TABLE 7

| ACTIVITY OF ANTIBIOTIC A-33853 | | |
|---|---|---|
| | Zone Diameter (mm.) at µg/disc | |
| Test Organism | 300 | 30 |
| *Staphylococcus aureus* 3055* | 11 | 10 |
| *Staphylococcus aureus* 3074** | 11.6 | 10.4 |
| *Staphylococcus aureus* 3130*** | 13.4 | 13.2 |
| *Streptococcus pyogenes* C203 | 8.0 | 0 |

*benzylpenicillin-susceptible
**benzylpenicillin-resistant
***benzylpenicillin-resistant, methicillin-resistant

AGAR-DILUTION SCREENING PROCEDURE

The agar-dilution procedure described by the International Collaborative Study (ICS) group was used to determine MIC values.

The results obtained from tests of antibiotic A-33853 in the agar-dilution screening procedure are given in Table 8, which follows:

TABLE 8

| ACTIVITY OF ANTIBIOTIC A-33853 | |
|---|---|
| Test Organism | MIC (µg/ml) |
| *Staphylococcus aureus* 3055* | 2 |
| *Staphylococcus aureus* 3074** | 2 |
| *Salmonella typhosa* SA12 | 2 |

*benzylpenicillin-susceptible
**benzylpenicillin-resistant

Antibiotic A-33853 was also tested in vitro to determine the MIC in µg/ml against a number of bacterial organisms pathogenic to animals. The results are recorded in Table 9, which follows.

TABLE 9
ACTIVITY OF ANTIBIOTIC A-33853 vs. BACTERIA PATHOGENIC TO ANIMALS

| Test Organism | MIC ($\mu$g/ml) |
|---|---|
| Staphylococcus sp. | 3.12 |
| Streptococcus sp. | 6.25 |
| Pasteurella multocida | |
| (bovine) | 1.56 |
| (turkey) | 6.25 |
| Bordetella bronchiseptica | >50.0 |
| Eschericia coli | >50.0 |
| Salmonella dublin | >50.0 |
| Pseudomonas (animal) | >50.0 |
| Mycoplasma gallisepticum | 1.56 |
| Mycoplasma synoviae | 1.56 |
| Mycoplasma hyorhinis | 1.56 |
| Mycoplasma hyopneumoniae | <0.78 |
| Pseudomonas (fish) | 50.0 |
| Aeromonas liquefaciens | 3.12 |

In order to illustrate more fully the operation of this invention, the following examples are provided.

EXAMPLE 1

Preparation of First Stage Inoculum

A medium was prepared for use in the agar slant culture of Streptomyces sp. NRRL 12068:

| Ingredient | Amount (g/L.) |
|---|---|
| Dextrin | 8.0 |
| Enzyme-hydrolyzed casein | 2.0 |
| Beef extract | 1.0 |
| Yeast extract | 1.0 |
| KCl | 0.5 |
| $MgSO_4 . 7H_2O$ | 0.5 |
| $FeSO_4 . 7H_2O$ | 0.01 |
| Agar | 20.0 |
| Deionized $H_2O$ | q.s to 1.0 liter |

The pH of the medium was adjusted to 7.0 with 5 N aqueous sodium hydroxide before autoclaving.

Spores of Streptomyces sp. NRRL 12068 were inoculated on a nutrient agar slant made up of the above-identified ingredients, and the thus-inoculated slant was incubated for about 7 days at a temperature of about 34°-37° C. The mature slant culture was then covered with water and scraped with a sterile tool to loosen the spores and mycelium. One milliliter of the resulting spore suspension was used to inoculate 100 ml. of vegetative medium of the following composition.

| Ingredient | Amount (g/L.) |
|---|---|
| Glucose | 15.0 |
| Soybean meal | 15.0 |
| Corn-steep liquor | 10.0 |
| $CaCO_3$ | 2.0 |
| NaCl | 5.0 |
| Tap $H_2O$ | q.s. to 1.0 liter |

Adjust pH to 6.5 with 5 N aqueous sodium hydroxide.

The vegetative inoculum was incubated in a 250 ml. wide-mouth Erlenmeyer flask at about 30° C. for about 48 hours on a shaker rotating through an arc 2 inches in diameter at 250 RPM. This incubated medium is used either to inoculate small fermentors (the inoculum being approximately 1% per volume of medium) or to inoculate a second stage medium for the production of a larger volume of culture.

Fermentation of A-33853

Incubated second-stage medium (800 ml.) thus prepared was used to inoculate 100 liters of sterile production medium having the following composition:

| Ingredient | Amount (g/L.) |
|---|---|
| Tapioca dextrin | 70.0 |
| Corn meal | 5.0 |
| Meat peptone | 10.0 |
| $MgSO_4 . 7H_2O$ | 4.0 |
| $CaCO_3$ | 2.0 |
| Tap $H_2O$ | q.s to 100 liters |

The inoculated production medium was allowed to ferment in a 165-liter fermentation tank for about 3 to 5 days at a temperature of about 30° C. The fermentation medium was aerated with sterile air at the rate of 0.5 v/v/m and was stirred with conventional agitators at 300 RPM.

EXAMPLE 2

Separation of A-33853 Antibiotic

Whole fermentation broth (188 liters), obtained as described in Example 1, was filtered using 5% filter aid (Hyflo Supercel, a diatomaceous earth, Johns-Manville Products Corporation) in a filter press, to give 150 liters of filtrate. This filtrate was adjusted to pH 6.5 with 5 N aqueous hydrochloric acid. The adjusted broth was extracted with an equal volume of chloroform. This chloroform extract was concentrated to a volume of approximately 500 ml., whereupon a crystalline material separated. The crystals were filtered off, washed with a small volume of cold chloroform, and dried in vacuo to give 9.16 g. of crude antibiotic A-33853.

A sample of this crude A-33853 antibiotic was purified in the following manner.

A 1.0-g. sample of crude A-33853 was dissolved in 15 ml. of a 1:1 mixture of acetonitrile and aqueous 1 N sodium hydroxide. This solution was filtered, and the pH of the filtrate was adjusted to 7.0 with 1 N aqueous hydrochloric acid. This solution was extracted 4 times with equal volumes of chloroform. The chloroform extracts were combined, concentrated to a volume of about 10 ml. and added to approximately 100 ml. of methanol. This solution was concentrated in vacuo until a precipitate separated. The precipitate was collected by filtration, washed with a small volume of cold chloroform, and dried under vacuum to yield 423 mg. of light yellow-green crystals. This preparation appeared as a single spot on silica gel, 60F-254, 20×20 cm thin-layer-chromatography plates (Catalog No. 5765, AM Labs., Inc., Merck-Darmstadt), when developed in acetonitrile:water (9:1) and detected by bioautography using a strain of Staphylococcus aureus.

EXAMPLE 3

Preparation of Tetraacetyl A-33853

Antibiotic A-33853, 9.1 g., was dissolved in 136 ml. of hot anhydrous pyridine, and 204 ml. of acetic anhydride was added thereto. The resulting clear solution was allowed to stand at room temperature for about 3 days. The crystalline precipitate which formed was collected by filtration. The solid thus obtained was washed with cold acetone and dried in vacuo to give 8.78 g. of product. The filtrate was concentrated to dryness. The residue was dissolved in acetone, and again concentrated to dryness. This operation was repeated 3 times to give an additional 2.21 g. of product to make a total yield of 10.99 g. of crude product. A sample of the crude product was recrystallized from a mixture of chloroform and ethanol to yield a white, crystalline product having a melting point of about 184°–189° C. The product was identified as tetraacetyl A-33853 by use of elemental analysis, potentiometric titration, infrared, ultraviolet, NMR and mass spectra, and X-ray powder diffraction.

Analysis Calcd. for $C_{28}H_{21}N_3O_{10}$:

|   | Calculated | Found |
|---|---|---|
| C | 60.11 | 60.12 |
| H | 3.76 | 3.92 |
| N | 7.51 | 7.73 |
| O | 28.62 | 28.50 |

We claim:

1. The method of producing the A-33853 antibiotic having the structure

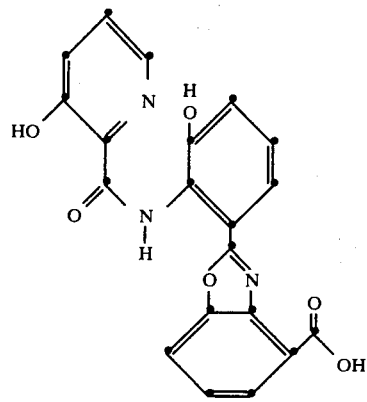

which comprises cultivating Streptomyces sp. NRRL 12068, or an A-33853-producing variant or mutant thereof, in a culture medium containing assimilable sources of carbon, nitrogen, and inorganic salts under submerged aerobic fermentation conditions until said antibiotic in the culture medium is produced.

2. The method of claim 1 which includes the additional step of isolating the A-33853 antibiotic from the culture medium.

* * * * *

UNITED STATES PATENT AND TRADEMARK OFFICE
CERTIFICATE OF CORRECTION

PATENT NO. : 4,293,649
DATED : October 6, 1981
INVENTOR(S) : Marvin M. Hoehn and Karl H. Michel It is certified that error appears in the above-identified patent and that said Letters Patent are hereby corrected as shown below:

Column 3, Table 2, line 3 under J column (Hz), "1.0; 7.8" should read --1.0; 8.8--.

Column 5, Table 6,

"a = 10.548 ± 0.001 A
b = 15.303 ± 0.003 A
c = 16.570 ± 0.003 A
β = 101.13 ± 0.01 A
ν = 2624.4 ± 0.8 A" should read --a = 10.548 ± 0.001 Å
b = 15.303 ± 0.003 Å
c = 16.570 ± 0.003 Å
β = 101.13 ± 0.01 Å
ν = 2624.4 ± 0.8 Å --.

Column 12, line 23, "antibiotic in the culture medium is produced" should read --antibiotic is produced in the culture medium--.

Signed and Sealed this

Thirtieth Day of March 1982

[SEAL]

Attest:

Attesting Officer

GERALD J. MOSSINGHOFF

Commissioner of Patents and Trademarks